United States Patent [19]

Weinshenker

[11] Patent Number: 5,068,227
[45] Date of Patent: Nov. 26, 1991

[54] CYCLODEXTRINS AS CARRIERS

[75] Inventor: Ned M. Weinshenker, Palo Alto, Calif.

[73] Assignee: Cyclex, Inc., New Brunswick, N.J.

[21] Appl. No.: 298,634

[22] Filed: Jan. 18, 1989

[51] Int. Cl.$^5$ .................... A61K 31/70; C08B 37/16; G01N 33/533
[52] U.S. Cl. .................... 514/58; 436/544; 436/56; 436/57; 436/86; 514/777; 514/778; 514/2; 424/1.1; 424/85.8; 424/88; 424/94.1
[58] Field of Search ............ 536/103; 514/58, 777, 514/778; 436/56, 57, 86, 544; 424/1.1, 85.8, 88, 94.1

[56] References Cited

U.S. PATENT DOCUMENTS

| 3,453,257 | 7/1969 | Parmerter | 536/46 |
|---|---|---|---|
| 4,334,069 | 6/1982 | Buckler et al. | 536/1.1 |
| 4,383,992 | 5/1983 | Lipari | 536/103 |
| 4,497,803 | 2/1985 | Harada et al. | 536/103 |
| 4,623,641 | 11/1986 | Szejtli et al. | 514/58 |
| 4,727,064 | 2/1988 | Pitha | 536/103 |
| 4,781,977 | 11/1988 | Yagi et al. | 536/103 |
| 4,834,985 | 5/1989 | Elger et al. | 424/488 |
| 4,870,060 | 9/1989 | Muller | 536/103 |
| 4,877,774 | 10/1989 | Pitha et al. | 514/58 |
| 4,877,778 | 10/1969 | Carpenter | 536/103 |
| 4,935,407 | 6/1990 | Luider et al. | 536/103 |
| 5,002,935 | 3/1991 | Bodor | 514/58 |

FOREIGN PATENT DOCUMENTS 197571 10/1986 European Pat. Off. .

OTHER PUBLICATIONS

Szejtli, *Cyclodextrins and Their Inclusion Complexes* 1982, Chinoin Research Center, Budapest Hungary, pp. 74–290.
Pitha et al., 1985, J. of Pharmaceutical Sciences 74 (9):987–990.

*Primary Examiner*—Ronald W. Griffin
*Attorney, Agent, or Firm*—Raymond S. Parker

[57] ABSTRACT

Cyclodextrins can be coupled to biorecognition molecules such as antibodies. The cyclodextrins so coupled provide a cavity or complexation zone into which active agents such as labels, drugs and the like may be incorporated. The active agent forms a noncovalently bonded inclusion complex within the cavity of the cyclodextrin. It remains associated with the cyclodextrin and the coupled biorecognition molecule and thus can be delivered to the other half of the biospecific recognition pair. A process for producing these materials is also disclosed. The process includes the steps of activating a primary hydroxyl site on a cyclodextrin; linking a biorecognition molecule to the activated primary hydroxyl site on the cyclodextrin in either a direct covalent linkage or through a covalently linked spacer; and introducing a guest molecule (active agent) into the cavity of the derivatized cyclodextrin to form an inclusion complex.

28 Claims, 13 Drawing Sheets

Scheme I

Scheme II

Scheme III

Scheme IV

Scheme IV

Scheme VI

Scheme VII

Scheme VIII

Scheme IX

Scheme IX CONT.

LI α-CD
LII β-CD
LIII γ-CD    +    LV    $\xrightarrow{pH6.9}$

LVI α-CD
LVII β-CD
LVIII γ-CD

F(ab')    +    LI
              LII
              LIII    $\xrightarrow{pH6.9}$

LIX
LX
LXI

IV α-CD
V β-CD
VI γ-CD

LXII α-CD
LXIII β-CD
LXIV γ-CD

LXV

Scheme X

Scheme X CONT.

CYCLODEXTRINS AS CARRIERS

BACKGROUND OF THE INVENTION

1. Field of the Invention

This invention relates to the use of cyclodextrins as carriers for active agents, for example drugs, labels, and the like. More specifically, it concerns the use of cyclodextrins as carriers for these active agents in combination with biospecific molecules such as proteins covalently bound to the cyclodextrins. The biospecific molecules facilitate delivery of the active agents to particular sites recognized by the biospecific molecules.

2. Background Information

The present invention employs cyclodextrins to carry active agents. Three monographs concerning cyclodextrins are *Cyclodextrins and Their Inclusion Complexes*, by J. Szejtli (Academiai Kiado, Budapest, 1962); *Proceeding of the 1st International Symposium on Cyclodextrins*, edited by J. Szejtli (D. Reidel Pub. Co., Dordrecht, Holland); and *Cyclodextrin Chemistry*, by M. L. Bender et al. (Springer-Verlag, Berlin, 1978). These three references provide a great deal of information on the preparation and properties of the cyclodextrin materials which are used as fundamental feedstocks in the present invention.

A number of systems have been proposed heretofore for delivering active agents to biologically recognizable sites. A "biologically recognizable site" is an organic group, usually a protein, or a molecule or larger organic structure which is capable of reacting with a second organic group, again usually a protein to form a unique complex. The wide range of events by which particular biologically recognizable sites uniquely complex with other molecules can include antibody-antigen interactions, hormone-receptor interactions, enzyme-substrate interactions and the like. The two groups which interact with one another can be termed a "biorecognition pair".

In these prior systems, the vector half of a biorecognition pair can carry an active agent such as a label, a drug, a toxin, or the like and through the biorecognition event specifically deliver this active agent to the other half of the pair which is present as part of an organism. In many cases heretofore, the active agent has been covalently bonded to the group which forms the vector half of the biorecognition pair. While this can work in some cases, in others, the cost and difficulties of making the covalent attachment are unacceptable, or the covalent attachment disturbs the properties of the active agent being delivered. In accord with the present invention, a universal carrier system is provided. This system has the advantage of not involving covalent bonding of the active agent to the biorecognition member.

Another advantage of this construction involves solubility issues. Many agents that are to be attached to biorecognition proteins are hydrophobic molecules. Their attachment decreases the solubility of the biorecognition molecule. Cyclodextrins confer increased solubility to the proteins and also help solubilize the complexed agent. Other hydroxyls on the cyclodextrins can be further derivatized to increase solubility if necessary.

STATEMENT OF THE INVENTION

It has now been found that cyclodextrin derivatives can be coupled to biorecognition molecules and that the cyclodextrin so coupled provides a cavity or complexation zone into which active agents such as labels, drugs and the like may be incorporated. The active agent forms a noncovalently bonded inclusion complex within the cavity of the cyclodextrin. The active agent remains associated with the cyclodextrin and the coupled biorecognition molecule and thus can be delivered to the other half of the biospecific recognition pair.

Thus, in one aspect, this invention concerns derivatized cyclodextrins of General Formula I.

Bap-Link-CD : GM

GENERAL FORMULA I

In General Formula I, CD represents the cyclodextrin; link represents a covalent linkage to the cyclodextrin through an hydroxyl site on the cyclodextrin. Link itself may be a covalent bond or it may be a spacer.

Bap represents the vector half of a biorecognition pair. That is, a molecule capable of entering into a specific recognition event with another organic structure. It is covalently bonded to link via a site that is not essential to its biorecognition activity. Bap may be a hormone, enzyme, antibody or any other biorecognition protein.

GM represents the guest molecule, that is the active agent which lodges in the cavity inside the cyclodextrin. GM is not covalently bonded to the cyclodextrin.

In another aspect, this invention provides a method for preparing the above materials. This method includes the steps of:

1. activating an hydroxyl site on a cyclodextrin;
2. linking a biorecognition molecule to the activated hydroxyl site on the cyclodextrin in either a direct covalent bond or through a covalently bonded spacer; and
3. introducing a guest molecule (active agent) into the cavity of the derivatized cyclodextrin to form an inclusion complex.

In other aspects, this invention concerns biorecognition molecules such as proteins covalently bonded to cyclodextrins either directly or through linking groups with the site of the coupling generally being hydroxyl groups which have been derivatized to active sites.

BRIEF DESCRIPTION OF THE DRAWINGS

The present invention will be described with reference made to the accompanying drawings in which.

DETAILED DESCRIPTION OF THE INVENTION

The Cyclodextrins

Figure 1C:
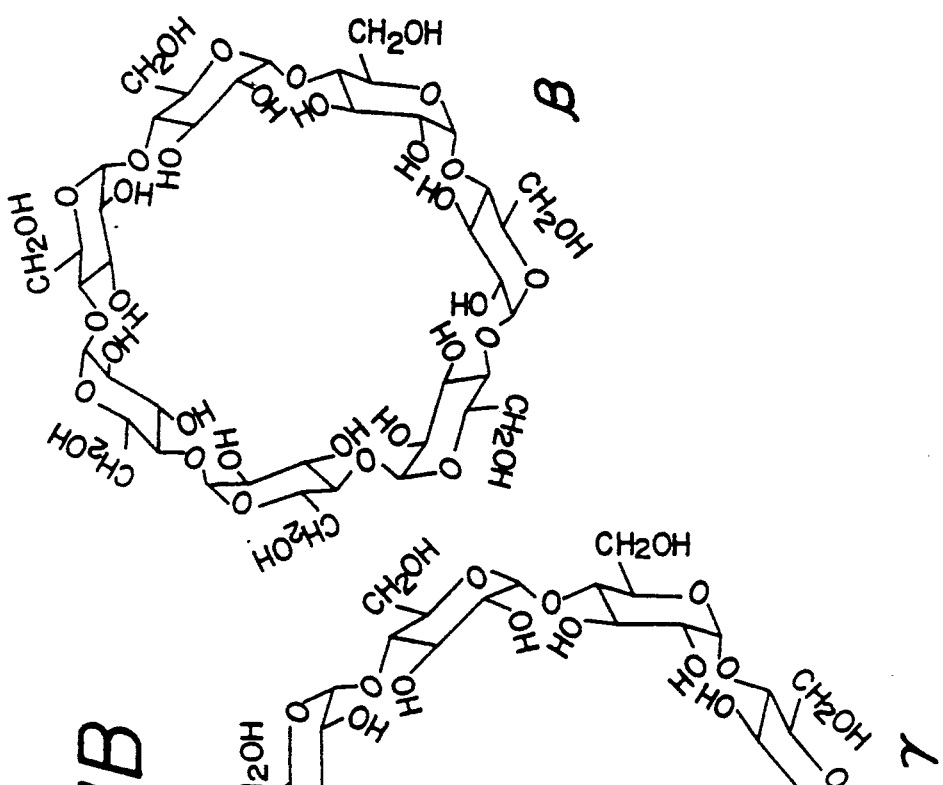
FIGS. 1A, 1B and 1C are a series of structural chemical formulae of three representative underivatized cyclodextrins useful in accordance with this invention.
Figure 1B:
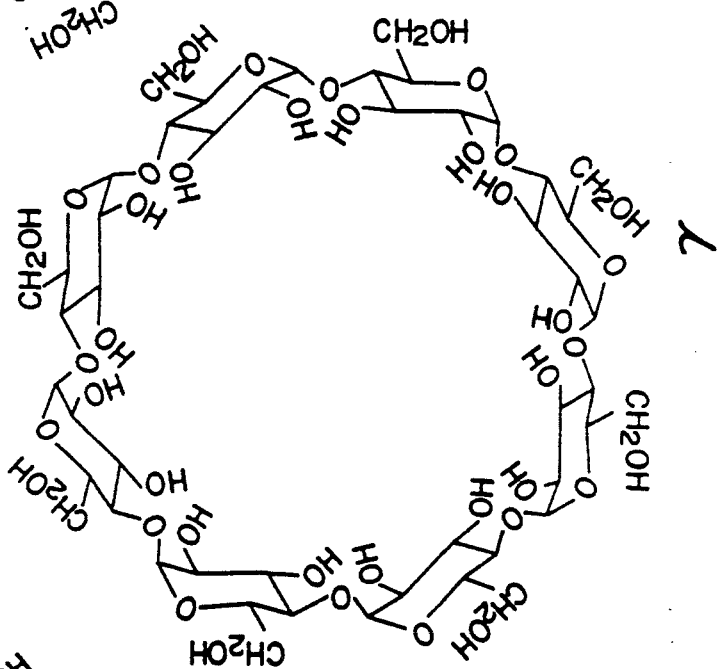
Figure 1A:
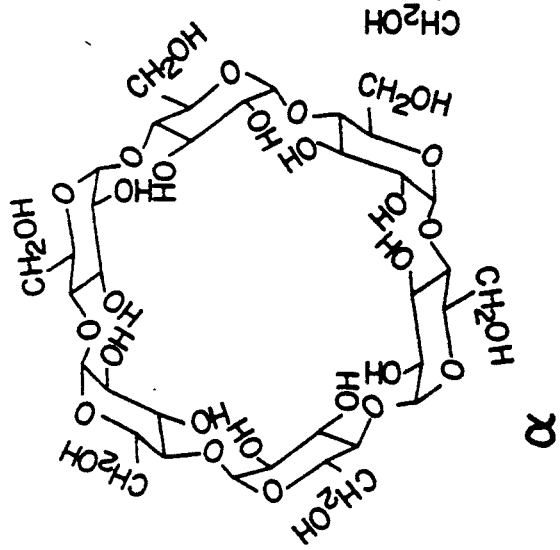
Figure 2:
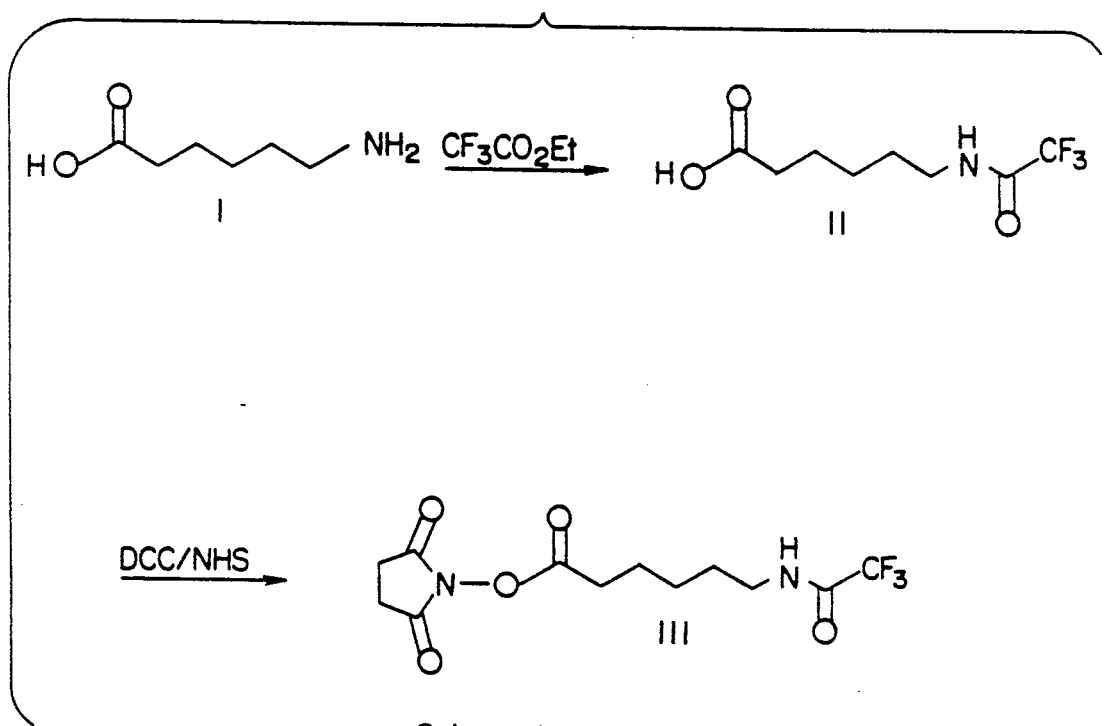
FIGS. 2-11 are chemical reaction schemes used to prepare representative materials of the present invention.
Figure 3:
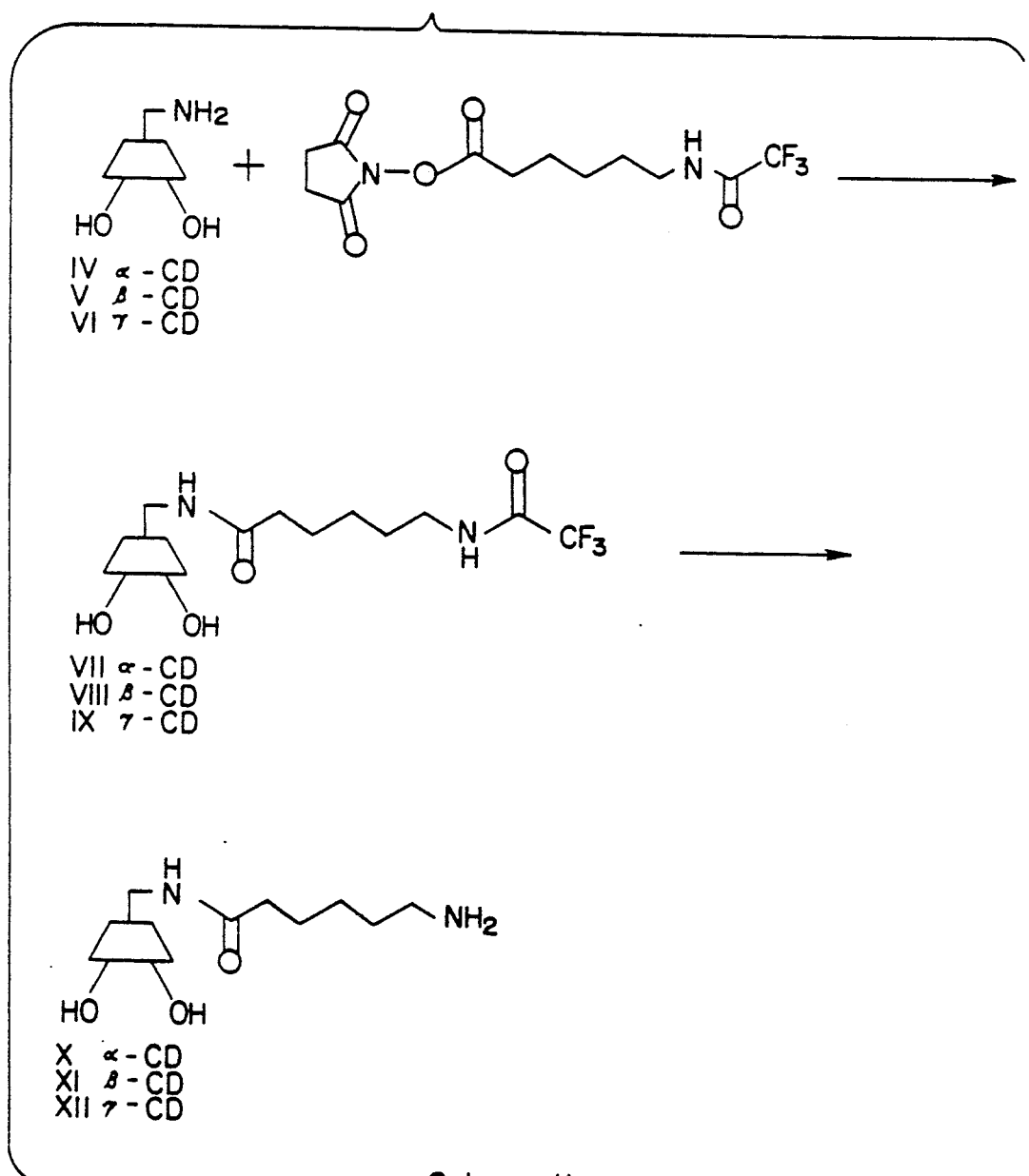
Figure 4:
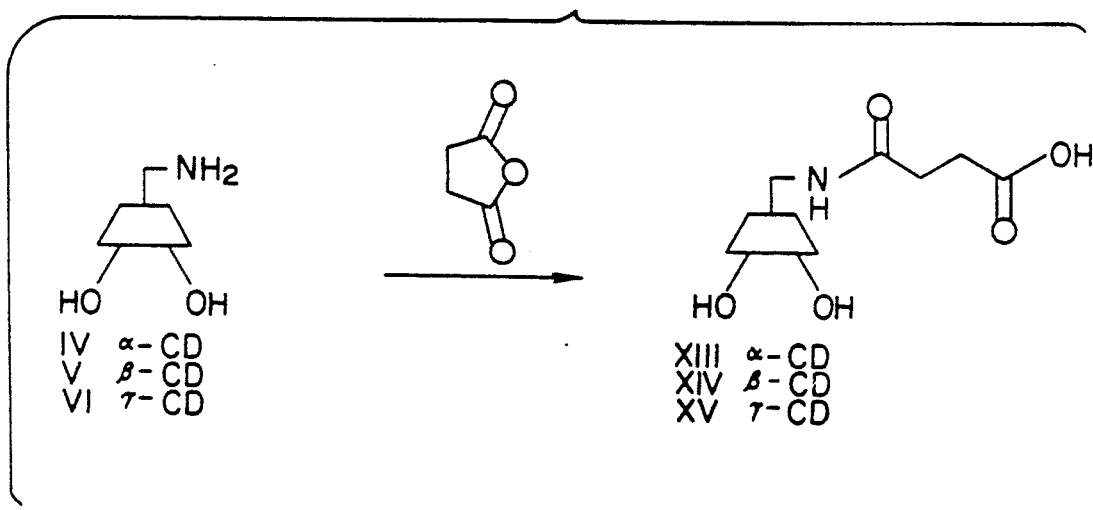
Figure 5:
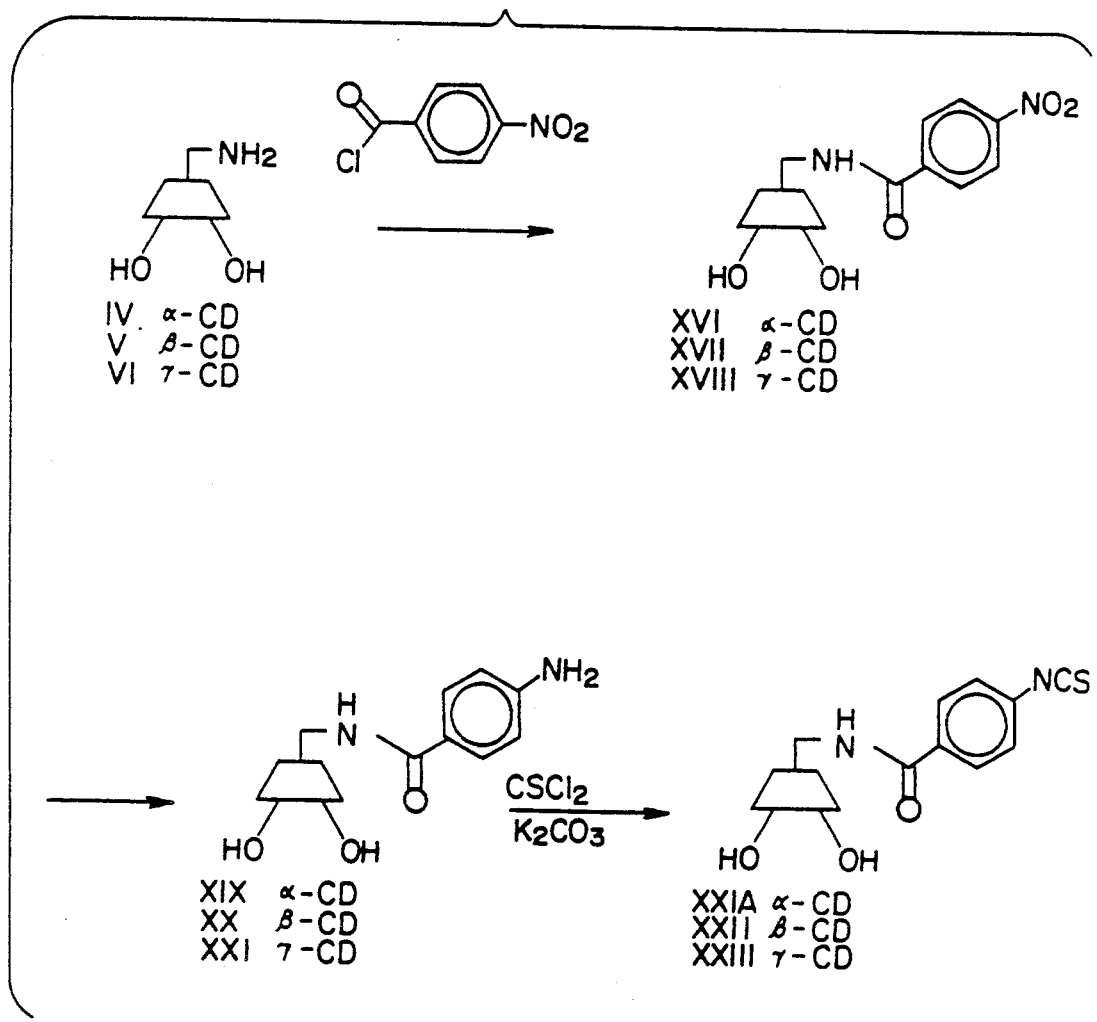
Figure 6:
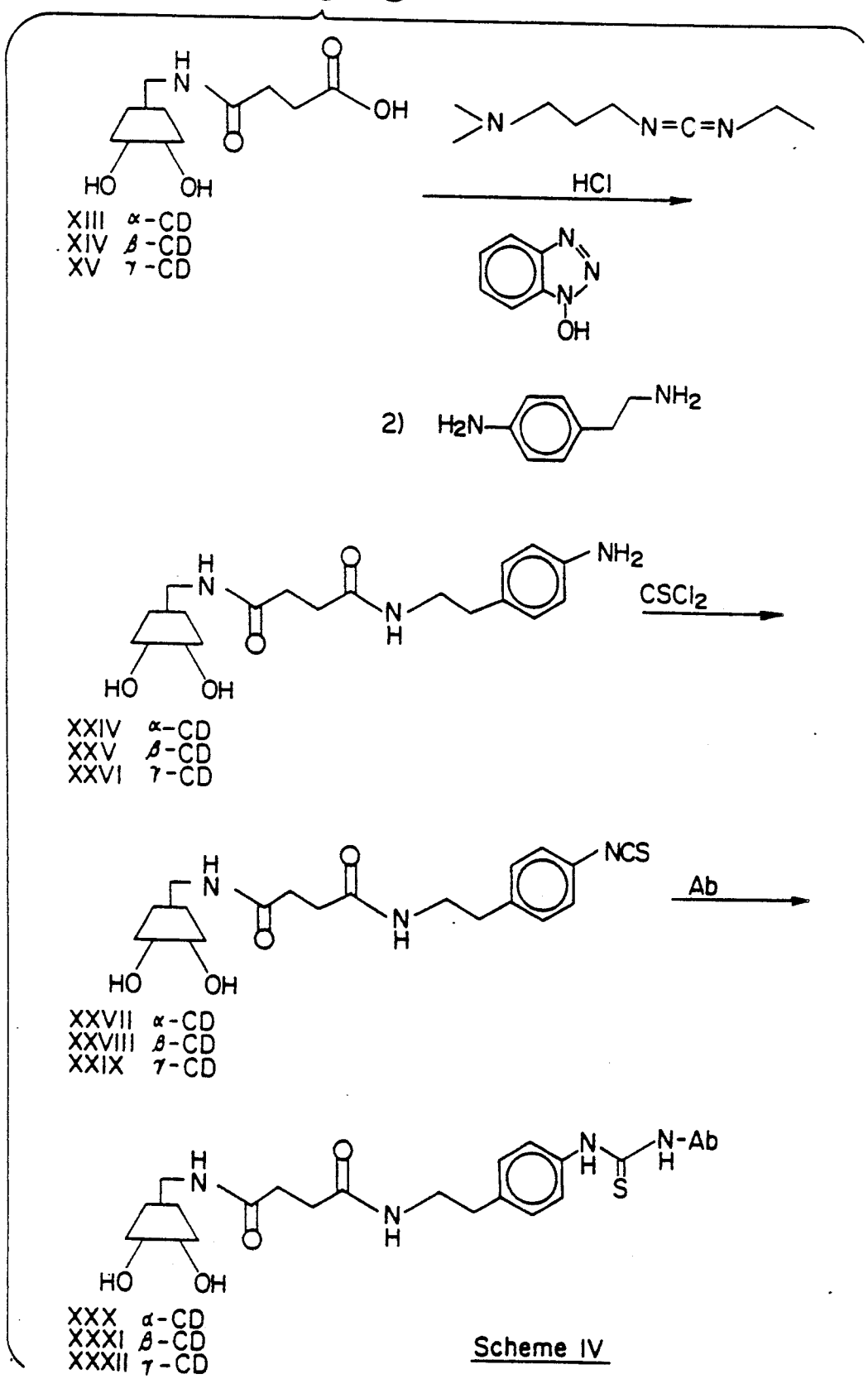
Figure 7:
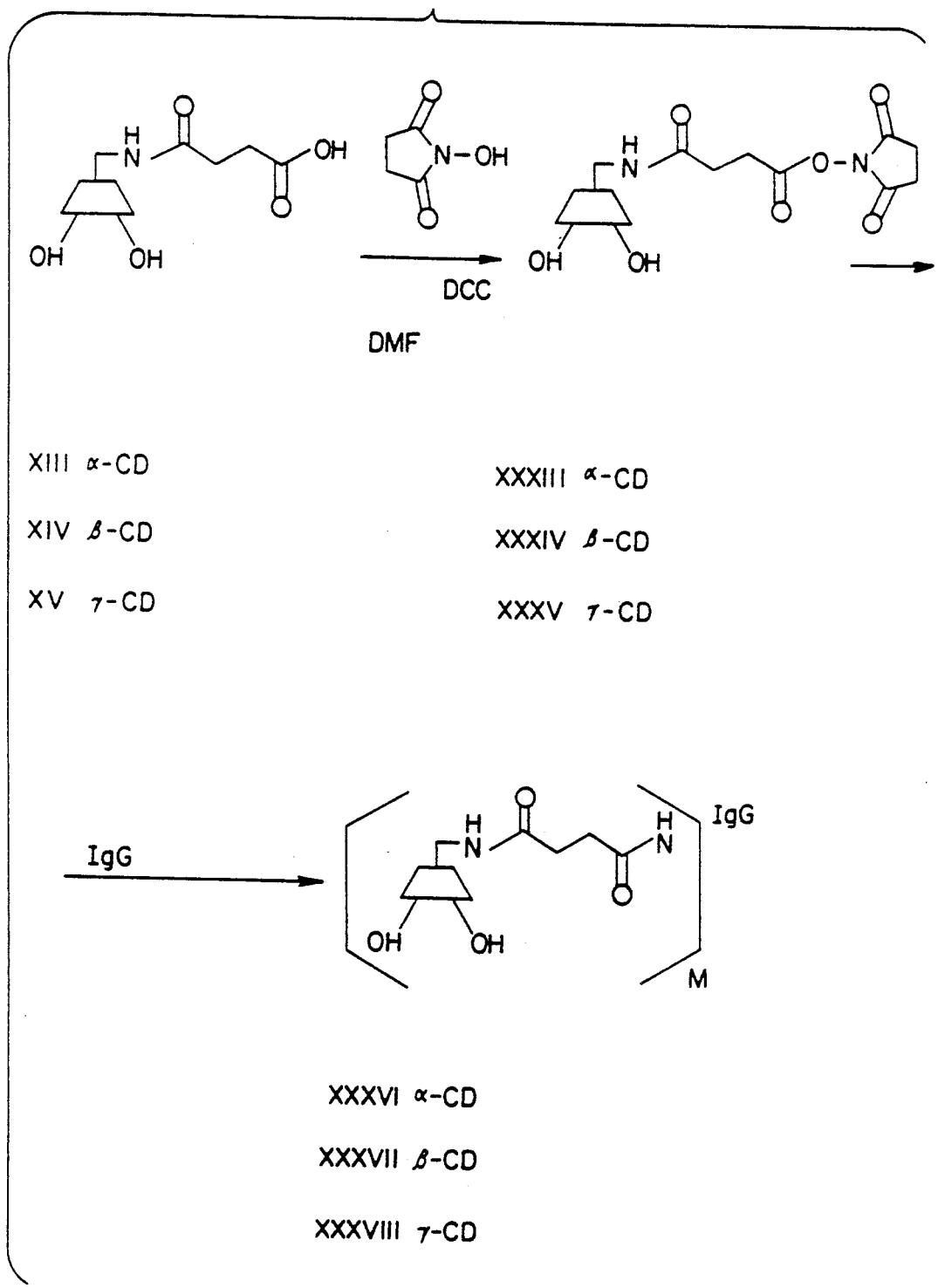
Figure 8:
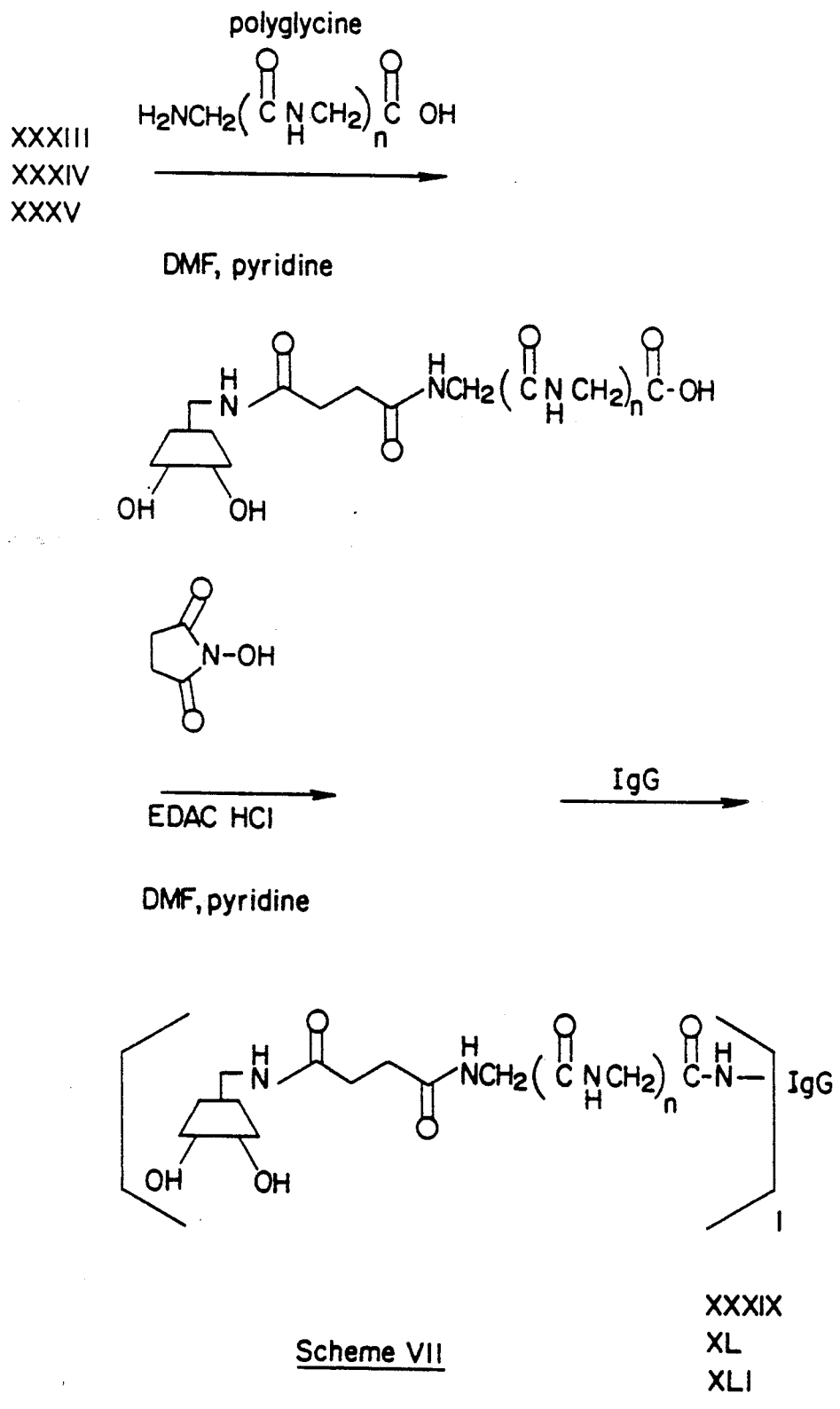
Figure 9:
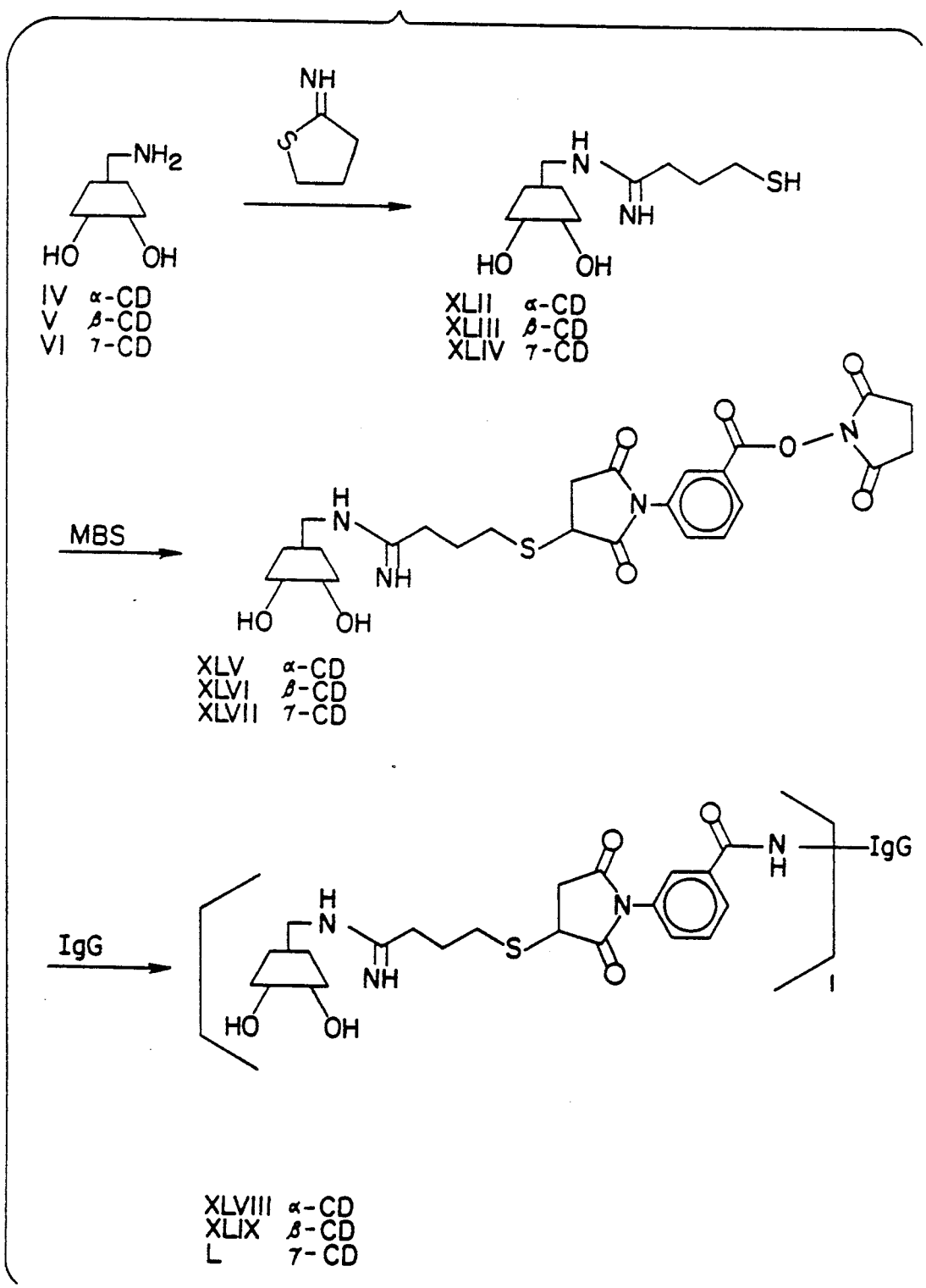
Figure 10:
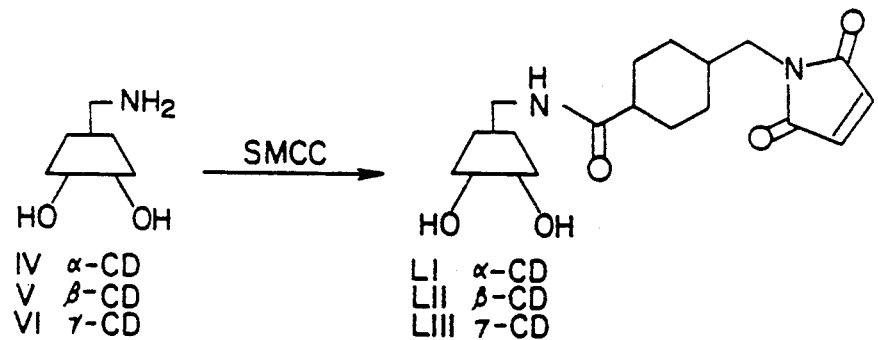
Figure 10:
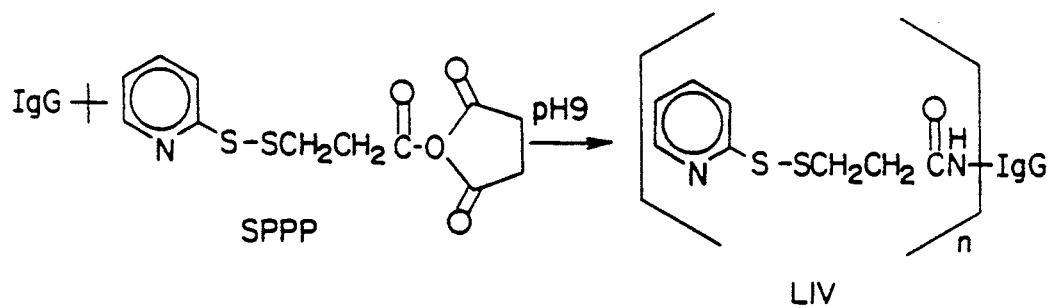
Figure 10:
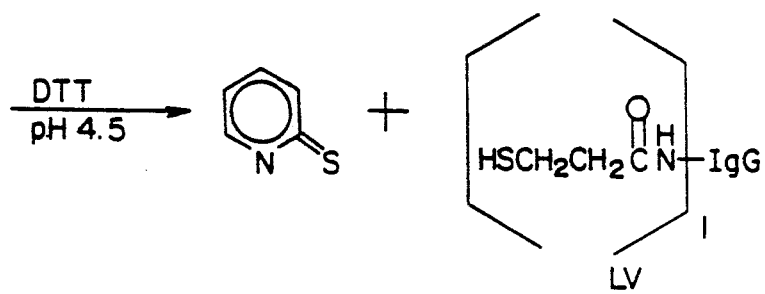
Figure 10:
Figure 10:
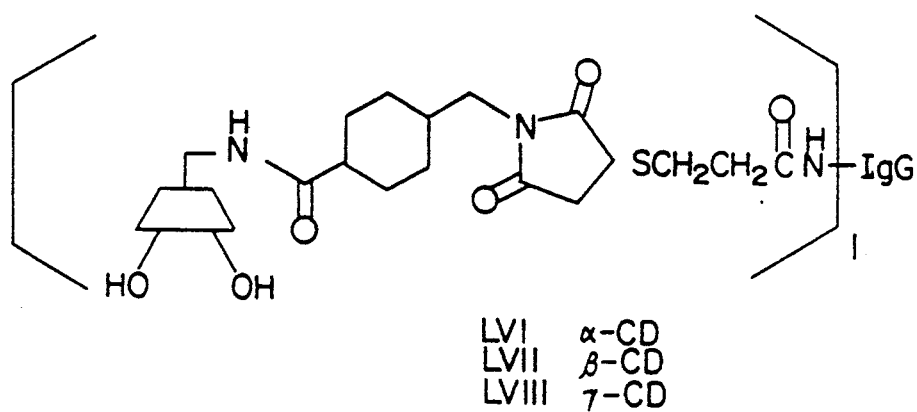
Figure 10:
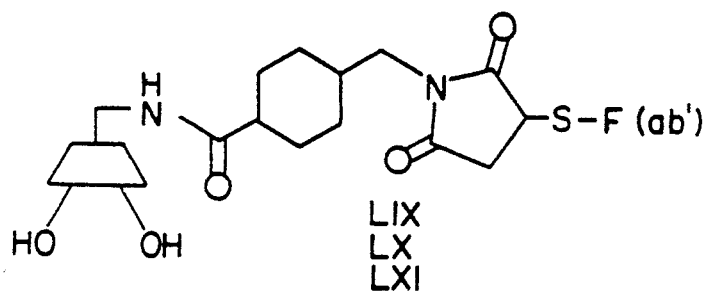
Figure 11:
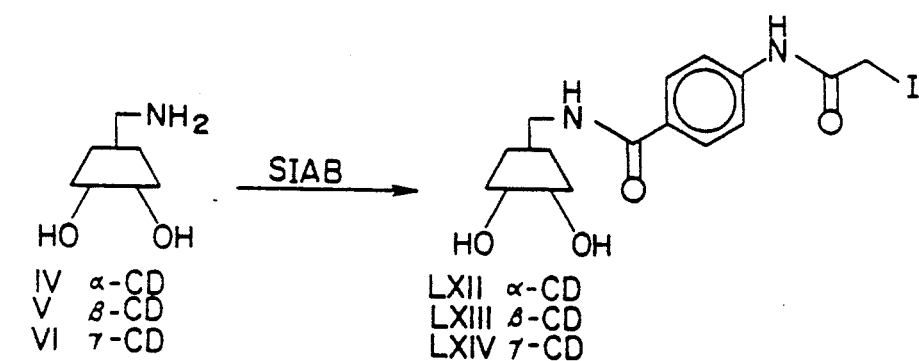
Figure 11:
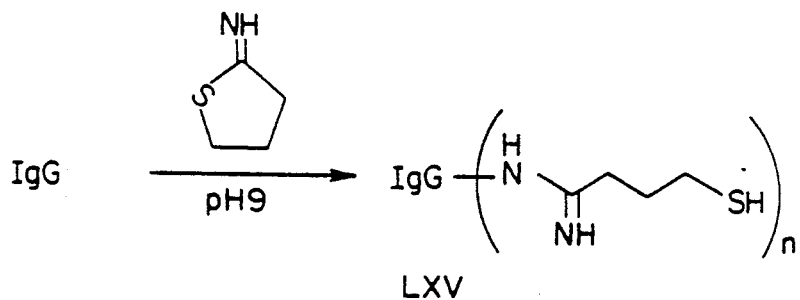
Figure 11:
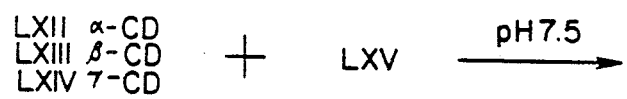
Figure 11:
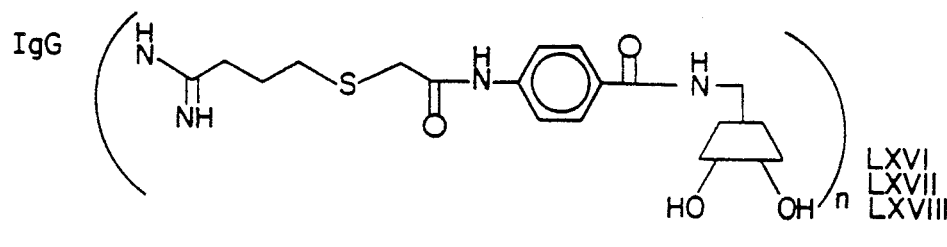
Figure 11:
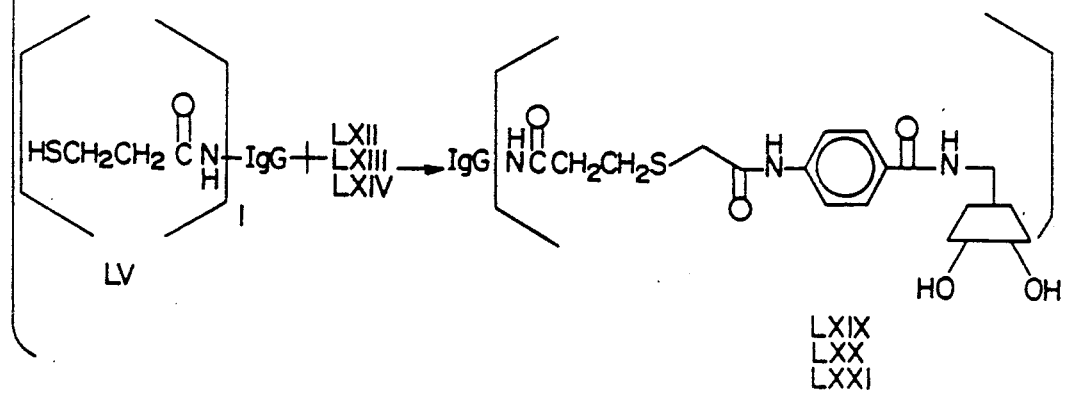

The present invention employs cyclodextrins as carriers for active agents. The cyclodextrins are a group of homologous oligosaccharides that are obtained from starch by the action of enzymes elaborated by *Bacillus macerans*. They are cyclic molecules containing six or more alpha-D-glucopyranose units linked together at the 1,4 positions as in amylose. This cyclic structure may also be referred to as a torus. FIGS. 1A, 1B and 1C show the structures of the three smallest cyclodextrins---alpha having six glucopyranose units, beta having seven glucopyranose units and gamma having eight glucopyranose units. Mixtures of these materials are included in the term "cyclodextrin" as used herein.

Alpha-cyclodextrin contains 18 hydroxyl groups and beta-cyclodextrin contains 21 hydroxyl groups, of which the primary ones (6 and 7, respectively) are the most reactive. Hydroxyls located on the secondary carbons, i.e., the ones at carbon 2 and carbon 3 also show a marked difference in their reactivity; the hydroxyls at carbon 3 being much less reactive than those at carbon 2. These various hydroxyl groups are all the possible derivatization points.

While it is possible to derivatize more than one hydroxyl, it is generally preferred to derivatize only one hydroxyl on each of the cyclodextrin molecules. This allows a more specific coupling of the biospecific protein molecule to the cyclodextrin and avoids cross-linking and denaturation of the often expensive bioactive molecule.

The usual coupling site on the cyclodextrin is the primary hydroxyl group located at the 6 position in the glucopyranose units. Thus, these derivatized materials are 6-deoxy,6-linked cyclodextrins.

The Linking Groups

The primary hydroxyl on the cyclodextrin is generally converted to an amine or to a carboxylic acid group so as to provide an active site for coupling. The addition of an amine may be carried out by methods known in the art for aminating polysaccharides, for example, the primary hydroxyl may be converted to the tosylate by reacting with p-toluene sulfonyl chloride; then displacing the tosylate with azide and then reducing the azide to an amine with an appropriate hydrogenation method such as with hydrogen and a noble metal catalyst.

A carboxyl can be introduced by oxidizing the hydroxyl with $Pt/O_2$ or $N_2O_4$ (Casu, B., Scovenna, G., Cifonelli, A. J., and Perlin, A. S., *Carbohydrate Research*, 63, 13 (1968)). However, these procedures lead to oxidation of all of the available primary hydroxyl groups. Monocarboxylic acid derivatives of -cyclodextrin have been prepared by Y. Kitaura and M. L. Bender, *Bioorganic Chemistry* 4, 237 (1975), by use of sodium iodoacetate in DMSO. This procedure introduces a single carboxymethyl group at the secondary hydroxyl groups.

The amine or carboxyl active site introduced into the cyclodextrin can be used as a site for direct attachment of the protein. More commonly, however, coupling agents are inserted between the cyclodextrin and the protein. These coupling agents are bifunctional groups which facilely and specifically couple to the two materials. They also can serve as spacers—separating the protein and carbohydrate spacially. They may be homobifunctional or heterobifunctional and may be selected from the wide range of materials known in the art as protein-carbohydrate coupling agents.

Typical coupling agents include maleimidoterminated chains, maleic and succinic anhydrides and their analogs, nitrobenzoyl chloride which is coupled at the acyl chloride group to cyclodextrin and then has its nitro group converted to an active isothiocyanate. Other groups capable of resulting in an active isothiocyanate can be used as well. Other representative coupling agents can include the heterobifunctional esters of N-hydroxysuccinimide shown in U.S. Pat. No. 4,253,996, the N-(4-carboxycyclohexylmethyl)malamido-N-hydroxysuccinimide esters as shown in S. Yoshitake et al., *Eur. J. Biochem.* 101, 395–399 (1979), the iodoacetyl-N-hydroxysuccinimide ester as set forth in E. Rector et al., *J. Immunol Methods*, 24, 321–336 (1978), bis-iminoesters, bis-diazotized benzidine, benzidine, glutaraldehyde, bisarylazides, bis-maleimides, active esters with carbamoyl and thiocarbamoyl groups, including the nitrogen and thio analogs thereof as described in U.S. Pat. Nos. 4,334,069; 4,323,647; and 4,046,636.

Typical spacers include polyols, polyamino acids such as polyglycines, and polyethers as well as derivatized long chain acids and alcohols. These materials are characterized as being divalent, so as to join the proteinaceous material to the cyclodextrin, and as not being adversely reactive with either the protein or the cyclodextrin. Typical spacers can include linear, branched and cyclic aliphatic groups as well as aromatic groups. Although not required, in general, spacers on the order of up to about 10 chain atoms long can be employed to assure the proper coupling of the bioactive protein to the cyclodextrin. Typical materials include the polyethylene glycols and the like.

The Biorecognition Molecule

The biorecognition molecules which are coupled to the cyclodextrin can be any material which is capable of entering into a biospecific recognition reaction. Thus, typical biorecognition molecules include proteins such as antibodies and antigens, hormones, cytokines, enzymes, receptors, as well as oligonucleotides, and the like. Typical antibodies can include monoclonal and polyclonal antibodies, fragments, and derivatives thereof. The peptides employed can be of natural or synthetic origin.

These biorecognition molecules can be selected from the following classes of materials as well as other related materials:

low molecular weight oligopeptides, such as di- through dodecapeptides;

macromolecular polyamino acids of from about 2000 to about 200,000 molecular weight including polypeptide hormones, enzymes, immunoglobulins and fragments thereof such as the Fab and Fc fragments and Bence-Jones proteins;

higher molecular weight proteins such as materials classed as protamines, histones, albumins, globulins, phosphoproteins, mucoproteins, lipoproteins, nucleoproteins, glycoproteins, and unclassified proteins such as insulin, somatotropin and prolactin.

Typical materials for coupling to the cyclodextrin can include albumin and prealbumin, antibodies to tumor cells or other disease states, alpha 1 lipoprotein, elastase inhibitors such as alpha 1 antitrypsin, transcortin, thyroxin-binding globulin, Gc-globulin, haptoglobin, erythropoietin, transferrin, hemopexin, plasminogen, immunoglobulin G, immunoglobulin M, immunoglobulin D, immunoglobulin E, immunoglobulin A, complement factors, prothrombin, parathyroid hormone, relaxin, glucagon, melanotropin, somatotropin, follicle stimulating hormone, luteinizing hormone, secretin, gastrin, oxytocin, vasopressin; enzymes such as cholinesterase, oxidoreductases, hydrolases, lyases and the like; interleukin such as IL-2; and growth factors such as EGF, TGF, and the like. These materials are merely representative of the types of materials which can be coupled to the cyclodextrins in accord with the present invention. Analogues and inhibitors derived from such materials are also encompassed by this invention.

The Guest Molecules

The guest molecules which can be included within the cyclodextrins can be selected from the wide variety of materials which will fit into the cavities provided by the cyclodextrin. These can include smaller, less branched molecules for inclusion in the alpha cyclodextrins, larger more branched materials for inclusion in the beta cyclodextrins and aromatics and other bulkier groups includable within the gamma cyclodextrins. The guest molecules have the advantage that they are not subjected to covalent bonding when inserted into the cavity of the cyclodextrin. This makes it possible for delicate materials not typically incorporated into covalently bound complexes and the like to be used.

The types of materials incorporated into the cavity of the cyclodextrins can be any type of molecule which will bring about a desired physical or chemical effect when incorporated in the cyclodextrin. This desired effect can be a label or reporter function which can be important when the bioactive protein locates and reacts with its bioactive mate. Similarly it can be a toxin or drug delivered specifically to a site of action by the biospecific reaction of the bound protein and its biospecific mate. Labels can include radiolabeled compounds such as carbon-14- or tritium-labeled materials ranging from simple alkyls or aryls to more complicated species. Other labels can include azo dyes, enzyme and coenzyme labels, fluorescent labels such as fluoresceins, rhodamines, rosamines, rare earth chelates, and the like, chemiluminescent compounds such as luminol and luciferin, chemical catalysts capable of giving a chemical indication of their presence, electron transfer agents and the like.

Active species which can be incorporated can include drugs, for example, alkaloids such as morphine, codeine and the like, ergot alkaloids, quinoline alkaloids and diterpene alkaloids. Steroids can be incorporated. Typical steroids include estrogens, androgens, adrenocortical steroids, as well as steroid mimics such as diethylstilbestrol. Lactams such as barbiturates can be incorporated as can aminoalkylbenzenes (amphetamines), benzheterocycles such as oxazepam and the like, vitamins such as A, B, C, D, E and K, prostaglandins, clofibric acid, indomethacin and other anti-inflammatory agents, growth factors, as well as other miscellaneous drugs, portions of which are capable of fitting into the cyclodextrin cavities.

Toxins and the like can include chlorambucil, melphalan, methotrexate, 5-fluorouracil, procarbazine, lectins and other materials known to have toxic properties to tissues or cells when delivered thereto.

Preparation Methods

As previously set forth, the compounds of the present invention are prepared by converting a primary hydroxyl on the cyclodextrin to an amine or carboxyl, activating this amine or carboxyl and then coupling the biorecognition protein followed by incorporating the guest molecule into the cyclodextrin cavity. These steps are described in the Examples.

Use of the Materials

The materials of this invention can be used to deliver labels, drugs, toxins and other guest molecules to biological sites identified by the biorecognition proteins bound to the cyclodextrins. Thus typical uses can be to deliver labels and drugs to disease sites in the body such as to tumors, arterial blockages, infections, and the like. Other uses can include use in assays and tests where the guest molecule provides a signal or other reporting event. Examples of these uses are intravenous or I.P. delivery of a solution of a drug or label to a patient such as a weekly administration by I.V. drip of from 0.01 to 0.1 mg/kg of a drug- or label-containing cyclodextrin-protein material with the protein having antibody properties to a $CD_4$ receptor on $T_4$ lymphocyte or the like. Such a therapy could deliver a drug or a label to that receptor and its associated tissues.

The material could also be used in in vitro tests such as labels on cell sorters and the like. A feature to be stressed in any of these uses is that the presence of the cyclodextrin can achieve a protein label (or drug) combination which is water soluble when many prior methods of labeling proteins interfere with their solubility.

The invention will be further described with reference being made to the following examples. These are provided merely to illustrate modes for practicing the invention and are not to be construed as limitations on the scope of the invention. In these examples, reference will be made to the sixteen journal articles now listed. These articles provide information on the various reactions carried out in the examples and are incorporated herein by reference.

References

1. Milton, L. D., and Slessor, K. N., *Carbohydrate Research*, 18, 29 (1971).
2. Tabushi, I., Shimizu, N., Sugimoto, T., Shiozuka, M., and Yamamura, K., *J Amer Chem Soc*, 99, 7100 (1977).
3. Curphey, T., *J Org Chem*, 44, 2805 (1979).
4. Carlsson, J., Drevin, H., and Axen, R., *Biochem J*, 173, 723-737 (1978).
5. Anderson, G., et al., *J Amer Chem Soc*, 86, 1839 (1964).
6. Newman, H., *J Org Chem*, 30, 1287 (1965).
7. Sharma, S., *Synthesis*, 803 (1978).
8. Staros, J., et al., *Anal Biochem*, 156 220 (1986).
9. King, T., Li, Y. and Kachoumian, L., *Biochemistry*, 17, 1499 (1978).
10. Yoshitake, S., et al., *S. Biochem*, 92 1413 (1982).
11. (a) Mahan, D., et al., *Anal Biochem*, 162, 163 (1987); (b) Yoshitake, S., et al., *Eur J Biochem*, 101, 395 (1979).
12. (a) Carlsson, J., et al., *Biochem J*, 173, 723 (1978); (b) Thorpe, P. E., et al., *Eur J Biochem*, 116, 447 (1981).
13. Kato, K., Fukui, H., Hamaguchi, Y., and Ishikawa, E., *J Immunol* 116, 155A (1976).
14. Weltman, J., Johnson, S., Langevin, J., and Liester, E., *BioTechniques*, 148 (1983).
15. Kulkarni, P. N., Blair, A. H., and Ghose, T. I., *Cancer Research* 41, 2700 (1981).
16. Casu, B., Scovenna, G., Cifonelli, A. J., and Perlin, A. S., *Carbohydrate Research*, 63, 13 (1968).
17. Kitaura, Y., and Bender, M. L., *Bioorganic Chemistry* 4, 237 (1975).

EXAMPLE 1

Preparation of mono-6-amino-6-deoxy-beta-cyclodextrin

A. Preparation of mono-6-tosyl-beta-cyclodextrin

This material is prepared by a modification of the procedure reported for the preparation of 6-tosyl-alpha-cyclodextrin (Milton, L. D., et al., *Carbohydrate Re-*

*search* (1971) 18:29). Anhydrous beta-cyclodextrin (beta-CD) (11.92 g, 10.5 mmole) is dissolved in pyridine (75 ml) on warming and the resulting solution is then cooled to −10° C. Solid tosyl chloride (3.01 g, 15.76 mmole) is then added and the reaction mixture stirred at 0°-5° C. for 25 hours. A second batch of tosyl chloride (3.00 g, 15.74 mmole) is then added and stirring continued at 5° C. overnight. Finally, a third batch (2.05 g, 10.75 mmole) is added and the reaction mixture is stirred at 5° C. for an additional 5 hours. TLC analysis at this point indicated about 50% conversion of the beta-CD to monotosylate with only minor amounts of poly-tosylated products. The solution is treated with methanol (10 ml) at 0° C. with stirring for 30 minutes to destroy the excess tosyl chloride and then diluted with chloroform (150 ml). The resulting precipitated solids are removed by filtration, washed with chloroform (150 ml) and vacuum dried to give 15.2 g of crude product. Recrystallization from hot water (100 ml) gave 5.50 g of product of greater than 90% purity by TLC (silica gel, 1 N acetic acid/methanol/methyl ethyl ketone (MEK) 5:3:12, with development by spraying with acetic acid-/anisaldehyde/methanol/sulfuric acid 45:2:430:22, mono-tosylate $R_f$ 0.61, beta-CD $R_f$ 0.42). Further recrystallization from ethanol and again from water gives 1.67 g of essentially pure product, m.p. 168°-172° C., reported 160°-162° C. (Tabushi, I., et al., *J Amer Chem Soc* (1977) 99:7100).

B. Preparation of 6-azido-6-deoxy-beta-cyclodextrin

Sodium azide (900 mg) is added to a solution of 6-tosyl-6-deoxy-beta-CD (1.30 g, 1.0 mmole) in dimethylformamide (DMF, 80 ml) and the mixture is heated with stirring at 100° C. for 1.5 hours. Analysis by TLC (silica gel, 1 N acetic acid/methanol/MEK, 5:3:12) indicated complete conversion to the azide ($R_f$ 0.54). The solution is cooled to room temperature and the excess sodium azide removed by centrifugation and rinsed with DMF (5 ml). The combined supernatants are concentrated in vacuo and the residue is dissolved in water (10 ml). The product is precipitated by addition of acetone (30 ml) and the solids are collected by centrifugation and vacuum dried to give 1.03 g of the azide (88.8% yield, m.p. ~250° C. dec.).

C. Preparation of 6-amino-6-deoxy-beta-cyclodextrin

A solution of the 6-azido-6-deoxy-beta-CD (1.02 g, 0.879 mmole) in water (80 ml) and methanol (20 ml) is prepared and 10% palladium on carbon catalyst (360 mg) added and the reaction mixture is stirred under a hydrogen atmosphere for 40 minutes. TLC analysis (silica gel, 1 N acetic acid/methanol/MEK, 5:3:12) indicated complete conversion to the amine ($R_f$ 0.23). The catalyst is removed by filtration through Celite and the filtrate is concentrated on the rotary evaporator. The residue is dissolved in DMF (20 ml), evaporated to dryness and triturated with acetone. The resulting white solids are removed by centrifugation, washed with acetone (2×15 ml) and dried in vacuo to give 990 mg of amine (0.873 mmole, 99% yield, m.p.~230° C. dec.).

EXAMPLES 2 and 3

Preparation of mono-6-amino-6-deoxy-alpha-cyclodextrin and mono-6-amino-6-deoxy-gamma-cyclodextrin The mono-alpha-derivative is prepared according to the procedure of Example 1 using alpha cyclodextrin as starting material. The mono-gamma-derivative is prepared similarly.

EXAMPLE 4

Coupling an Active Ester to an Amine-Derivatized Cyclodextrin

A. Preparation of 6-trifluoroacetamidocaproic Acid (II)

Ethyl trifluoroacetate (7.1 g, 50 mmole) is added with stirring to a suspension of 6-aminocaproic acid (I, 5.0 g, 40 mmole) in methanol (25 ml) and triethylamine (40 mmole) is added, with stirring. After stirring for 12 hours, by which time all the acid is in solution, the mixture is diluted with methylene chloride (100 ml) and made acidic (pH 1) with 1 N HCl. Saturated sodium chloride solution (90 ml) is then added and the lower layer is separated. The aqueous layer is extracted with methylene chloride (100 ml) and the two organic extracts are combined, dried over sodium sulfate and the solvents evaporated to afford 5.21 g of the desired acid II (Scheme I).

B. Preparation of 6-trifluoroacetamidocaproic Acid N-hydroxysuccinimide Ester (III)

Dicyclohexylcarbodiimide (2.7 g, 13 mmole) is added to a solution of the acid II (3.0 g, 13 mmole) and N-hydroxysuccinimide (1.5g, 13 mmole) in ethyl acetate (30 ml) at 0° C. The mixture is allowed to come to room temperature and is then stirred overnight. The resulting dicyclohexylurea is removed by filtration and washed with ethyl acetate. The filtrate is rotary evaporated to dryness to yield 4.1 g of the ester III (Scheme I).

C. Preparation of (6-((6-trifluoroacetamido)-hexanamido)-6-deoxy)-alpha-cyclodextrin (VII)

The active ester III (0.324 g, 1 mmole) is slowly added to a solution of (6-amino-6-deoxy)-cyclodextrin (1.0 g, 1 mmole) in DMF (20 ml) at ice-bath temperature. The stirred solution is allowed to come to room temperature overnight and then rotary evaporated to dryness. The residue is dissolved in a small amount of DMF and added dropwise to a large excess of ether. The desired precipitated product is then collected by filtration.

D. Preparation of (6-(6-aminohexanamido)-6-deoxy)-alpha-cyclodextrin (X)

To a solution of the amido-alpha-cyclodextrin VII above (1.0 g, 0.85 mmole) in water (50 ml) is added potassium carbonate (117.5 mg, 0.85 mmole) and the resulting mixture is stirred for 12 hours at room temperature. The solution is then rotary evaporated to dryness and the residue treated with DMF (5 ml). The insoluble salts are removed by filtration and the supernatant is added dropwise to a large excess of ether. The precipitated product is isolated by filtration and dried. This process is repeated twice to ensure removal of undesired salts.

EXAMPLE 5

Preparation of (6-(6-aminohexanamido)-6-deoxy)-betacyclodextrin (XI)

The preparation of the amino-alpha-cyclodextrin X of Example 4 is substantially repeated with the change that an equivalent amount of (6-amino-6-deoxy)-betacyclodextrin (V) is substituted for (6-amino-6-deoxy)-alpha-cyclodextrin to produce the intermediate amido cyclodextrin VIII and the final product XI which are the analogs of the products IX and X as shown in Scheme II.

EXAMPLE 6

Preparation of [6-(6-aminohexanamido)-6-deoxy)-gamma-cyclodextrin (XII)

The preparation of the amino-alpha-cyclodextrin X of Example 4 is substantially repeated with the change that an equivalent amount of (6-amino-6-deoxy)-gammacyclodextrin (VI) is substituted for (6-amino-6-deoxy)-alpha-cyclodextrin IV to produce the intermediate amido cyclodextrin IX and the final product XII which are the analogs of the products VII and X as shown in Scheme II.

EXAMPLE 7

Preparation of (6-(3-carboxypropanamido)-6-deoxy)-alphacyclodextrin (XIII) Active Couplinq Species Succinic anhydride (0.1 g, 1 mmole) is added to a solution of (6-amino-6-deoxy)-alpha-cyclodextrin (1.0 g, 1 mmole) in pyridine (30 ml) at ice-bath temperature. After stirring 15 minutes the mixture is allowed to come to room temperature and stirring is continued for 12 hours. The solution is then rotary evaporated to dryness and the residue is dissolved in DMF (4 ml). This solution is added dropwise to a large excess of ether. The precipitated product is collected and dried at high vacuum.

EXAMPLES 8 and 9

Preparation of (6-(3-carboxypropanamido)-6-deoxy)-betacyclodextrin (XIV) and (6-(3-carboxypropanamido)-6-deoxy-gamma-cyclodextrin (XV)

The preparation of the carboxy-alpha-cyclodextrin XIII of Example 7 is substantially repeated with the change that an equivalent amount of (6-amino-6-deoxy)-beta-cyclodextrin (V) or (6-amino-6-deoxy)-gammacyclodextrin (VI) is substituted for (6-amino-6-deoxy)-alpha-cyclodextrin IV such that the final products, XIV and XV respectively, are the analogs of the product XIII as shown in Scheme III.

EXAMPLE 10

Introduction of Isothiocyanato Active Coupling Site Into Cyclodextrin

A. Preparation of (6-(4-nitrobenzamido)-6-deoxy)-alphacyclodextrin (XVI)

4-nitrobenzoyl chloride (186 mg, 1 mmole) is slowly added to a solution of (6-amino-6-deoxy)-alphacyclodextrin (1.0 g, 1 mmole) in pyridine (30 ml) at ice-bath temperature. The reaction mixture is allowed to stir at room temperature overnight, rotary evaporated to dryness and the residue dissolved in DMF (5 ml). The solution is then added dropwise with stirring to a very large excess of chloroform. The precipitated product is removed by filtration and the process repeated twice to remove pyridine and pyridine hydrochloride and then dried a high vacuum.

B. Preparation of (6-(4-aminobenzamido)-6-deoxy)-alphacyclodextrin (XIX)

To a solution of nitro-alpha-cyclodextrin XVI (500 mg, 0.45 mmole) in water (100 ml) is added 150 mg of palladium black. The nitro compound is reduced under one atmosphere of hydrogen on a Parr hydrogenator for 12 hours at room temperature. The catalyst is removed by filtration and the filtrate rotary evaporated to dryness to obtain the desired amine XIX.

C. Preparation of (6-(4-isothiocyanatobenzamido)-6-deoxy)-alpha-cyclodextrin (XXIA)

A solution of thiophosgene (53 mg, 0.46 mmole) in chloroform (15 ml) is added to a solution of the anilino-alpha-cyclodextrin XIX (500 mg, 0.46 mmole) in 100 ml of water which contains 63 mg of potassium carbonate. The heterogeneous mixture is rapidly stirred at room temperature for 3 hours and then the phases are allowed to separate. The lower organic phase is removed and the aqueous phase is rotary evaporated to dryness. The residue is treated with DMF (3 ml) and the insoluble inorganic salts removed by filtration. The DMF solution is then added dropwise to a large excess of ether with stirring and the precipitated product collected by filtration. This is repeated two more times to remove salts and the desired isothiocyanate XXIA is then dried at high vacuum.

EXAMPLES 11 AND 12

Preparation of (6-(4-isothiocyanatobenzamido)-6-deoxy)-beta-cyclodextrin (XXII) and (6-(4-isothiocyanatobenzamido)-6-deoxy)-gamma-cyclodextrin (XXIII)

The preparation of the isothiocyanato-alphacyclodextrin XXI of Example 10 is substantially repeated with the change that an equivalent amount of (6-amino-6-deoxy)-beta-cyclodextrin (V) or (6-amino-6-deoxy)-gammacyclodextrin (VI) is substituted for (6-amino-6-deoxy)-alpha-cyclodextrin. The intermediates thus formed (the nitro-cyclodextrin XVII and the anilino-cyclodextrin XX or the nitro-cyclodextrin XVIII and the anilino-cyclodextrin XXI as well as the final products (XXII or XXIII) are the analogs of the products XVI, XIX and XXIA as shown in Scheme IV.

EXAMPLE 13

Preparation of (6-(4-(4-aminophenethylamino)-4-oxo-butanamido)-6-deoxY)-alpha-cyclodextrin (XXIV)

1-hydroxybenzotriazole (143 mg, 1.1 mmole) is added to a solution of the alpha-cyclodextrin carboxylic acid XIII (1.07 g, 1 mmole) in pyridine (30 ml). This is then followed by the addition of 1-(3-dimethylamino-propyl)-3-ethylcarbodiimide hydrochloride (240 mg, 1.25 mmole). The resulting mixture is stirred at room temperature for 1 hour after which 2-(4-aminophenyl)ethylamine (136 mg, 1 mmole) is added. This solution is stirred at room temperature for 12 hours, rotary evaporated to dryness and the residue treated with DMF (4 ml). Insoluble material is removed by filtration and the DMF filtrate added dropwise with stirring to a large excess of ether. The precipitated product is collected and dried in high vacuum.

EXAMPLE 14

Preparation of (6-(4-isothiocyanatophenethylamino)-4-oxobutanamido)-6-deoxY)-alpha-cyclodextrin (XXVII)

The procedure employed here is analogous to the synthesis of the isothiocyanato-alpha-cyclodextrin XXIA shown in Example 10. In this case 0.5 g (0.42 mmole) of the anilino-alpha-cyclodextrin XXIV of Example 13, 48 mg (0.42 mmole) of thiophosgene and 58 mg (0.42 mmole) of potassium carbonate are used as starting materials. This preparation is repeated using beta- and delta-cyclodextrin in place of alpha to give corresponding materials XXVIII and XXIX.

EXAMPLES 15-17

Coupling Proteins to Derivatized Cyclodextrins

EXAMPLE 15

Preparation of Conjugate XXX

A freshly prepared DMF solution (100 μl) of the isothiocyanate XXVII (prepared by dissolving 6.07 mg of XXVII in 500 ul of distilled DMF) is added slowly to a solution containing monoclonal antibody VIM-C6 (5 mg, $3.33 \times 10^{-8}$ mole) in 2 ml of 0.1 M borate buffer at pH 9.0. This monoclonal antibody is capable of differentiating human leukocytes of the granulocytic form. The solution is stirred at 0° C. for 2 hours and then at room temperature for an additional 4 hours. The reaction mixture is then transferred to a dialysis tubing and dialyzed against three changes of two liters each of pH 7.4 phosphate-buffered saline (PBS) over a 24 hour period.

EXAMPLES 16 AND 17

Preparation of Conjugates XXXI and XXXII

The reaction of Example 15 is repeated with the change that equivalent amounts of isothiocyanates XXVIII or XXIX are substituted for isothiocyanate XXVII such that the final conjugates XXXI and XXXII, respectively, are obtained as analogs of the conjugate XXX as shown in Scheme V.

EXAMPLES 18-20

Coupling of a Protein to Cyclodextrins Via a Spacer Link

EXAMPLE 18

A. Preparation of (6-(3-(succinimidylcarboxy)-propanamido)-6-deoxy)-alpha-cyclodextrin (XXXIII)

To a solution of 528 mg (9.5 mmole) of 6-(3-carboxypropanamido)-6-deoxy-alpha-cyclodextrin (XIII) in 15 ml of DMF is added 60.3 mg (0.52 mmole) of N-hydroxysuccinimide and 113.5 mg (0.55 mmole) dicyclohexylcarbodiimide. The reaction mixture is stirred at room temperature for 6 hours. The precipitate of dicyclohexyl urea is removed by filtration and the filtrate concentrated in vacuo. The residue is treated with methylene chloride (30 ml) and the precipitated product is collected and dried in vacuum. This product of the active ester XXXIII is used without further purification.

B. Preparation of (6-(3-(succinimidylcarboxy)-propanamido)-6-deoxy)-beta-cyclodextrin (XXXIV) and (6-(3-(succinimidylcarboxy)-propanamido)-6-deoxy)-gamma-cyclodextrin (XXXV)

The preparation of (6-(3-(succinimidylcarboxy)-propanamido)-6-deoxy)-alpha-cyclodextrin (XXXIII) is repeated with the change that an equivalent amount of 6-(3-carboxypropanamido)-6-deoxy-beta-cyclodextrin (XIV) or 6-(3-carboxypropanamido)-gamma-cyclodextrin (XV) is substituted for the 6-(3-carboxypropanamido)-6-deoxy-alpha-cyclodextrin XIII such that the final active esters, XXXIV and XXXV respectively, are prepared as analogs of the product XXXIII as shown in Scheme VI.

C. Preparation of Conjugate XXXVI

The active ester XXXIII (5.8 mg, 5 μmole) is dissolved in 500 μl DMF and 100 μl of this solution (1 μmole) is added slowly to a solution of IgG (5 mg, $3.33 \times 10^{-8}$ mole) in 2 ml of 0.1 M borate buffer (pH 9.0) at 0° C. The reaction mixture is stirred gently at 0° C. for 2 hours, then transferred to a dialysis tubing and dialyzed against three changes of two liters of PBS (pH 7.4) solution over a 24 hour period.

EXAMPLES 19-20

Preparation of Conjugates XXXVII and XXXVIII

The preparation of conjugate XXXVI is repeated with the change that equivalent amounts of active esters XXXIV or XXXV are substituted for the active ester XXXIII such that the final conjugates XXXVII and XXXVIII, respectively, are the products analogous to XXXVI as shown in Scheme VI.

EXAMPLE 21

Preparation of (IgG-polyglycine-6-(3-carboxypropanamido)-6-deoxy-alpha-cyclodextrin) Conjugate XXXIX A solution of 6-(3-(succinimidylcarboxy)-propanamido)-6-deoxy-alpha-cyclodextrin (57.6 mg, 50 umole), prepared as in Example 18, in DMF (1 ml) is added to a solution of poly-1-glycine (200 mg, 50 umole, mol. wt. 4000) in a mixture of pyridine (0.3 ml) and DMF (2 ml). The reaction mixture is stirred at room temperature for 2 hours and then N-hydroxysuccinimide (63.2 mg, 55 μmole) and 1-(3-dimethylaminopropyl)-3-ethylcarbodiimide hydrochloride (133.7 mg, 70 μmole) are added to the reaction mixture. The reaction mixture is stirred at room temperature for 4 hours. The final volume of the solution is adjusted to 10 ml with DMF to give a $5 \times 10^{-3}$ molar concentration of the intermediate active ester. This DMF solution (200 μl) is added slowly to a stirred solution of murine anti-L1210 monoclonal antibody (5 mg, $3.33 \times 10^{-8}$ mole) in 2 ml of 0.1 M borate buffer (pH 9.0) at 0° C. The reaction mixture is stirred gently at 0° C. for 2 hours and then transferred to a dialysis tubing and dialyzed against three changes of two liters of PBS (pH 7.4) solution over a period of 24 hours.

EXAMPLE 22

Preparation of IgG-polyqlycine-6-(3-carboxypropanamido)-6-deoxy-beta-cyclodextrin) Conjugate XL and IgG-polyglycine-6-(3-carboxypropanamido)-6-deoxy-gamma-cyclodextrin) Conjugate XLI The preparation of conjugate XXXIX of Example 19 is repeated with the change that equivalent amounts of active esters XXXIV or XXXV are substituted for the active ester XXXIII to produce the final conjugates XL and XLI, respectively, which are analogous to conjugate XXXIX as shown in Scheme VII.

EXAMPLE 23

A. Preparation of [6-(4-thiobutyramidino)-6-deoxy]-alphacyclodextrin XLII

As illustrated in Scheme VIII, 2-iminothiolane (13 mg, 0.1 mmole) is added to a solution of (6-amino-6-deoxy)-alpha-cyclodextrin IV (100 mg, 0.1 mmole) in pyridine (3 ml) at room temperature. After stirring for 1 hour the solution is rotary evaporated to dryness and the residue dissolved in DMF (2 ml). This solution is added dropwise to a large excess of chloroform to precipitate the product which is collected by filtration. The process is repeated twice to remove pyridine and pyridine hydrochloride and the product is dried at high vacuum.

B. Preparation of the N-hydroxysuccinimide Activated Ester XLV

To a solution of the thiol XLII (100 mg, 0.09 mmole) in DMF (5 ml) is added m-maleimidobenzoyl-N-hydroxysuccinimide ester (MBS, 29.5 mg, 0.09 mmole). The mixture is stirred for 2 hours at room temperature and then rotary evaporated to dryness. The residue is dissolved in DMF (3 ml) and the resulting solution is added dropwise to a large excess of chloroform with stirring. The precipitated product is removed by filtration, the process repeated once more, and the final product dried under high vacuum.

C. Preparation of Conjugate XLVIII

A freshly prepared DMF solution (100 ul) of active ester XLV (1.38 mg, 1 μmole) is added to a solution of anti-CEA IgG (5 mg, $3.33 \times 10^{-8}$ mole) in 2 ml of 0.1 M borate buffer (pH 9.0). The solution is stirred at 0° C. for 2 hours and then transferred to a dialysis tubing and dialyzed against three changes of two liters each of PBS (pH 7.4) over a period of 24 hours.

EXAMPLES 24–25

Preparation of Conjugate XLIX and L

The preparation of conjugate XLVIII is repeated with the change that equivalent amounts of active esters XLVI or XLVII are substituted for the active ester XLV to produce the final conjugates XLIX and L respectively, as analogs of conjugate XLVIII as shown in Scheme VIII.

EXAMPLE 26

Preparation of [6-(4-maleimidomethylcyclohexanecarbox amido)-6-deoxy]-alpha-cyclodextrin (LI) (11)

Succinimidyl-4-(N-maleimidomethyl) cyclohexane-1-carboxylate (SMCC, 33.4 mg, 0.1 mmole) is added to a solution of (6-amino-6-deoxy)-alpha-cyclodextrin IV (100 mg, 0.1 mmole) in DMF. After stirring at room temperature for 1 hour the mixture is rotary evaporated to dryness. The residue is dissolved in DMF (2 ml) and the resulting solution is added dropwise to a large excess of ether with stirring. The process is repeated and the precipitated product is collected by filtration and dried under high vacuum.

EXAMPLES 27–28

Preparation of [6-(4-Maleimidomethylcyclohexanecarbox amido)-6-deoxy]-beta-cyclodextrin (LII) and 6-(4-maleimidomethylcyclohexanecarboxamido)-6-deoxy]-gammacyclodextrin (LIII)

The preparation of the maleimido-alphacyclodextrin LI is substantially repeated with the change that an equivalent amount of (6-amino-6-deoxy)-betacyclodextrin (V) or (6-amino-6-deoxy)-gamma-cyclodextrin (VI) is substituted for (6-amino-6-deoxy)-alphacyclodextrin (IV). The products LII or LIII are analogous to the product LI as shown in Scheme IX.

EXAMPLE 29

A. Preparation of 2-Pyridyldithiopropionylated IgG LIV (12)

A solution (80 ul, 20 mmole) of N-succinimidyl-3-(2-pyridyldithio)propionate is added at 0° C. to a stirred solution of IgG (10 mg, $6.67 \times 10^{-8}$ mole) in 2 ml of 0.1 M borate buffer (pH 9.0). The reaction mixture is stirred at 0° C. for 30 minutes and then at room temperature for 1 hour. The solution is applied to a column (1×10 cm) of Sephadex G-25 (8 ml) which has been equilibrated with 0.1 M sodium acetate (pH 4.5) and the derivatized IgG is eluted with the same buffer. The IgG-containing fractions are then pooled (2.7 ml). One portion of the solution is analyzed by the method of Carlsson et al. (11a). An average of about 15 mole of 2-pyridyldithio group are introduced per mole of antibody.

B. Preparation of Thiopropionylated IgG LV

Dithiothreitol (10 mg) is added to 2.5 ml of 0.1 M acetate buffer (pH 4.5) containing 8 mg of 2-pyridyldithiopropionylated IgG derivative LIV. The solution is stirred for 30 minutes at room temperature and then applied to a column (1.5×6.5 cm) of Bio-Gel P-6DG. The gel is pre-equilibrated with 0.1 M phosphate buffer (pH 7.5) containing 0.1 M NaCl which has been deoxygenated with a stream of nitrogen. Further elution with nitrogen-flushed phosphate buffer gives the thiopropionylated IgG (ca. 3.5 ml).

C. Preparation of Conjugate LVI

A freshly prepared DMF solution (20 mmole) of the maleimido-alpha-cyclodextrin derivative LI is added at 0° C. to the freshly prepared and stirred solution of thiopropionylated IgG LV (8 mg, $5.33 \times 10^{-8}$ mole) in 3.5 ml phosphate buffer (pH 7.5). The reaction mixture is stirred at 0° C. overnight and then dialyzed against three changes of two liters each of PBS (pH 7.5) solution over a 24 hour period.

EXAMPLES 30–31

Preparation of Conjugates LVII and LVIII

The preparation of conjugate LVI is repeated with the change that equivalent amounts of maleimido derivatives LII or LIII are substituted for the maleimido derivative LI. The final conjugates LVII and LVIII, respectively, are analogous to conjugate LVI as shown in Scheme IX.

EXAMPLE 32

Preparation of Conjugate LIX

F(ab')₂ antibody fragments are prepared from IgG using Pierce ImmunoPure F(ab')₂ preparation kit. Dithiothreitol (DTT, 3.96 mg) is added to a solution (1 ml) of F(ab') (3 mg, $3 \times 10^{-8}$ mole) in pH 6.9 phosphate buffer and the reaction mixture is stirred under argon for 1 hour (13). The DTT is removed on a Bio-Gel P-6DG column (1×7 cm) which is pre-equilibrated with PBS containing 1 mM EDTA. The F(ab,) (about $6 \times 10^{-8}$ mole in 2.3 ml) obtained is treated with 50 μl of 15 mM maleimide derivative LI in DMF at 0° C. under argon. The reaction mixture is stirred at 0° C. overnight and then dialyzed three times against one liter of PBS over a 24 hour period.

EXAMPLES 33-34

Preparation of Conjugates LX and LXI

The preparation of conjugate LIX is repeated with the change that equivalent amounts of maleimido derivatives LII or LIII are substituted for the maleimido derivative LI. The final conjugates LX and LXI, respectively, are analogous to conjugate LIX as shown in Scheme IX.

EXAMPLE 35

Preparation of [6-(4-iodoacetamido)benzamido-6-deoxy]-alpha-cyclodextrin LXII (14)

A solution of N-succinimidyl-(4-iodoacetyl-)aminobenzoate (SIAB, 40.2 mg, 0.1 mmole) in 1 ml of DMF is added slowly to a solution of (6-amino-6-deoxy)-alphacyclodextrin IV, (100 mg, 0.1 mmole) in DMF (10 ml). After stirring for 1 hour at room temperature the mixture is rotary evaporated to dryness and the residue dissolved in a small amount of DMF (4 ml) and this solution is added dropwise to a large excess of ether with stirring. The precipitated product is removed by filtration, treated once more by the above procedure and then dried under high vacuum.

EXAMPLES 36-37

Preparation of [6-(4-iodoacetamido}benzamido-6-deoxy]-beta-cyclodextrin (LXIII) and [6-(4-iodoacetamido)benzamido-6-deoxy]-gamma-cyclodextrin (LXIV)

The preparation of the iodoacetyl-alphacyclodextrin LXII is substantially repeated with the change that equivalent amounts of (6-amino-6-deoxy)-betacyclodextrin (V) or (6-amino-6-deoxy)-gamma-cyclodextrin (VI) are substituted for (6-amino-6-deoxy)-alphacyclodextrin IV. The products LXIII or LXIV are the analogs of the product LXII as shown in Scheme X.

EXAMPLE 38

A. Preparation of thiobutyramidinated IgG (LXV)

A freshly prepared aqueous solution (40 mM, 90 ul) of iminothiolane (9) is added to a stirred solution of IgG (10 mg, $6.67 \times 10^{-8}$ mole) in 2 ml of 0.1 M borate buffer (pH 9.0). The reaction mixture is stirred at room temperature for 2 hours and the amidinated IgG is separated from reagent by passing the solution through a Bio-Gel p-6DG column (1.5×6 cm) equilibrated with 100 mM phosphate buffer (pH 7.5) containing 1 mM disodium EDTA. Elution with argon-flushed phosphate buffer gives thiobutyramidinated-IgG LXV (35 ml). The number of thio groups present is determined by spectrophotometric titration of the amidinated IgG with 1 mM 4,4'-dithiopyridine (15).

B. Preparation of Conjugate LXVI (14)

A freshly prepared DMSO solution (50 μl, 40 mM) of iodoacetyl derivative LXII is added to a stirred solution of amidinated IgG LX (10 mg) in 3.5 ml of 0.1 M phosphate buffer (pH 7.5). The reaction mixture is stirred at room temperature for three hours and then dialyzed against three changes of two liters each of PBS solution over a 24 hour period.

EXAMPLES 39-40

Preparation of Conjugate LXVII and LXVIII

The preparation of conjugate LXVI is repeated with the changes that equivalent amounts of iodoacetyl derivatives LXIII or LXIV are substituted for the iodoacetyl derivative LXII. The final conjugates LXVII and LXVIII, respectively, are the analogs of conjugates LXVI as shown in Scheme X.

EXAMPLE 41

Preparation of Conjugate LXIX

A freshly prepared DMSO solution (50 μl, 20 mM) of iodoacetyl derivative LXII is added to a stirred solution of freshly prepared thiopropionylated IgG (LV) (5 mg) in 2 ml of 0.1 M phosphate buffer (pH 7.5). The reaction mixture is stirred at room temperature for 4 hours under argon and then dialyzed against three changes of two liters each of phosphate buffer (pH 7.4) over a 24 period.

EXAMPLES 42-43

Preparation of Conjugate LXX and LXXI

The preparation of conjugate LXIX is repeated with the changes that equivalent amounts of iodoacetyl derivatives LXIII or LXIV are substituted for the iodoacetyl derivative LXII. The final conjugates LXX and LXXI, respectively, are the analogs of conjugate LXIX as shown in Scheme X.

EXAMPLE 44

Preparation of Inclusion Complex of Methotrexate with Antibody Conjugate XL

Methotrexate is an antimetabolite used in the treatment of certain neoplastic diseases. The advantages of linking the drug to an anti-tumor antibody have been demonstrated in vivo in mice (15). A solution of methotrexate in alkaline saline (55 mM, 12 μl, $6.7 \times 10^{-7}$ moles) is added to 1 ml of a 0.1 M phosphate buffer (pH 7.5) solution of conjugate XL (10 mg, $6.7 \times 10^{-8}$ moles). After stirring at room temperature for four hours the solution is fractionated on a TSK HW55s gel permeation column using PBS as eluant. The molar ratio of methotrexate to antibody in fractions where the two materials co-elute is determined by spectroscopic comparison of the absorption at 302 nm for methotrexate to that at 280 nm for the IgG using appropriate standard solutions of each.

EXAMPLE 45

Preparation of the Inclusion Complex of Floxuridine with the Antibody Conjugate XLVIII 2'-deoxy-5-fluorouridine is an antimetabolite useful in the treatment of metastatic carcinomas. It is a highly toxic drug with a narrow margin of safety and is effective at doses as low as 0.1 mg/kg making it an ideal candidate for antibody-directed specific delivery via an inclusion complex. Conditions required for formation of a 1:1 complex are established using radioactively labeled 5-fluorouridine-6-(3H). Thus, an aqueous solution of 2'-deoxy-5-fluorouridine (0.05 M, 6.5 μl, $3.3 \times 10^{-7}$ moles) is added to 1 ml of a 0.1 M phosphate buffer solution of conjugate XLVIII (5 mg, $3 \times 10^{-8}$ moles) and the solution stirred at room temperature for four hours. The solution is then fractionated on a TSK HW55s gel permeation column with elution by PBS.

EXAMPLE 46

Preparation of the Inclusion Complex of Chlorambucil with Conjugate XXX

Chlorambucil is an alkylating agent of the nitrogen mustard type which is useful in treatment of chronic lymphocytic leukemia, malignant lymphomas and Hodgkin's disease. Its high toxicity, low effective dosage (0.1 mg/kg), limited water solubility and hydrophobic character can benefit from delivery as a cyclodextrin inclusion complex. A 50 mM dioxane solution (5 µl, $2.5 \times 10^{-7}$ moles) is added to a solution of conjugate XXX (5 mg, $3.3 \times 10^{-8}$ moles) in 1 ml of PBS and allowed to stand at room temperature overnight. The mixture is then filtered through a 2 micron filter and separated on a TSK HW55s gel filtration column with elution by PBS.

What is claimed is:

1. An active agent-tagged biorecognition molecule comprising said biorecognition molecule covalently bonded to a cyclodextrin with said active agent noncovalently included within the cavity of the cyclodextrin.

2. The active agent-tagged biorecognition molecule of claim 1 wherein said biorecognition molecule is a protein.

3. The active agent-tagged protein of claim 2 wherein said cyclodextrin is alpha cyclodextrin.

4. The active agent-tagged protein of claim 2 wherein said cyclodextrin is beta cyclodextrin.

5. The active agent-tagged protein of claim 2 wherein said cyclodextrin is gamma cyclodextrin.

6. The active agent-tagged protein of claim 2 wherein the covalent bonding is to a carbon which bore a primary or secondary hydroxyl on the original cyclodextrin.

7. The active agent-tagged protein of claim 2 wherein the covalent bonding is to a hydroxyl on the cyclodextrin.

8. The active agent-tagged protein of claim 7 wherein the covalent bonding is to a secondary hydroxyl on the cyclodextrin.

9. The active agent-tagged protein of claim 6 wherein said hydroxyl has been converted to an amine.

10. The active agent-tagged protein of claim 6 wherein said hydroxyl has been converted to a carboxyl.

11. The active agent-tagged protein of claim 2 additionally comprising a spacer molecule covalently coupled between the protein and the cyclodextrin.

12. The active agent-tagged protein of claim 2 wherein said protein is a biorecognition protein.

13. The active agent-tagged protein of claim 12 wherein said active agent is a label.

14. The active agent-tagged protein of claim 12 wherein said active agent is a toxin.

15. The active agent-tagged protein of claim 12 wherein said active agent is a drug.

16. The active agent-tagged protein of claim 2 wherein said protein is an antibody.

17. The active agent-tagged protein of claim 16 wherein said antibody is a monoclonal antibody.

18. The active agent-tagged protein of claim 16 wherein said antibody is a polyclonal antibody.

19. The active agent-tagged protein of claim 10 wherein said active agent is a label.

20. The active agent-tagged protein of claim 10 wherein said active agent is a toxin.

21. The active agent-tagged protein of claim 10 wherein said active agent is a drug.

22. A method for preparing an active agent-tagged biorecognition molecule in which the biorecognition molecule is covalently bonded to a cyclodextrin with said active agent noncovalently included within the cavity of the cyclodextrin/includes the steps of:
   a) activating a hydroxyl site on a cyclodextrin;
   b) linking a biorecognition molecule to the activated hydroxyl site on the cyclodextrin in either a direct covalent linkage or through a covalently linked spacer to yield a derivatized cyclodextrin; and
   c) introducing an active agent as a guest molecule into the cavity of the derivatized cyclodextrin to form an inclusion complex.

23. The method of claim 22 wherein said biorecognition molecule is a biorecognition protein and activating comprises converting said hydroxyl to an amine.

24. The method of claim 23 wherein said cyclodextrin is alpha cyclodextrin.

25. The method of claim 23 wherein said cyclodextrin is beta cyclodextrin.

26. The method of claim 23 wherein said cyclodextrin is gamma cyclodextrin.

27. A method for delivering a drug to a patient suffering from a disease state comprising administering to said patient a material of claim 15 wherein the biorecognition protein has on its biorecognition pair a material related to the disease state.

28. In an assay method in which a labeled protein specifically conjugates its biorecognition pair, the improvement comprising using as the labeled protein the material of claim 13.

* * * * *